United States Patent
Baril

(10) Patent No.: US 11,596,467 B2
(45) Date of Patent: Mar. 7, 2023

(54) ARTICULATING TIP FOR BIPOLAR PENCIL

(71) Applicant: Covidien LP, Mansfield, MA (US)

(72) Inventor: Jacob C. Baril, North Haven, CT (US)

(73) Assignee: Covidien LP, Mansfield, MA (US)

( * ) Notice: Subject to any disclaimer, the term of this patent is extended or adjusted under 35 U.S.C. 154(b) by 376 days.

(21) Appl. No.: 16/781,557

(22) Filed: Feb. 4, 2020

(65) Prior Publication Data
US 2021/0236194 A1 Aug. 5, 2021

(51) Int. Cl.
*A61B 18/14* (2006.01)
*A61B 18/16* (2006.01)

(52) U.S. Cl.
CPC .......... *A61B 18/1445* (2013.01); *A61B 18/16* (2013.01); *A61B 2018/1412* (2013.01); *A61B 2018/1495* (2013.01)

(58) Field of Classification Search
CPC ................ A61B 18/1445; A61B 18/16; A61B 2018/1412; A61B 2018/1495; A61B 2018/00178; A61B 18/1402; A61B 2018/00601
See application file for complete search history.

(56) References Cited

U.S. PATENT DOCUMENTS

| | | |
|---|---|---|
| 2,022,065 A | 11/1935 | Wappler |
| 2,047,535 A | 7/1936 | Wappler |
| 3,516,412 A | 6/1970 | Ackerman |
| 3,886,944 A | 6/1975 | Jamshidi |
| 3,911,241 A * | 10/1975 | Jarrard .................... H01H 13/08 606/42 |
| 3,920,022 A * | 11/1975 | Pastor ................ A61B 18/1402 606/41 |
| 4,161,950 A | 7/1979 | Doss et al. |
| 4,170,234 A * | 10/1979 | Graham ............. A61B 18/1402 606/49 |
| 4,196,734 A | 4/1980 | Harris |

(Continued)

FOREIGN PATENT DOCUMENTS

| | | |
|---|---|---|
| WO | 2016025132 A1 | 2/2016 |
| WO | WO-2018162423 A1 * | 9/2018 |

OTHER PUBLICATIONS

U.S. Appl. No. 16/540,593 to Baril et al.

*Primary Examiner* — Thomas A Giuliani
*Assistant Examiner* — Ryan T Clark
(74) *Attorney, Agent, or Firm* — Carter, DeLuca & Farrell LLP

(57) ABSTRACT

An electrode assembly for an electrosurgical pencil includes an insulative housing. A locking plate is supported at a distal end of the insulative housing about a pivot, the locking plate including a series of locking holes defined therein. A tip assembly is coupled to a distal end of the locking plate and is configured to treat tissue. A connection is coupled to a proximal end of the insulative housing and is electrically coupled to the tip assembly. One or more locking fingers is operably disposed within the housing and is movable between a first position allowing rotation of the locking plate and the tip assembly about the pivot and a second position preventing rotation of the locking plate and the tip assembly. The finger(s) is configured to engage a corresponding one of the series of locking holes to prevent rotation of the locking plate and the tip assembly.

11 Claims, 6 Drawing Sheets

(56) References Cited

U.S. PATENT DOCUMENTS

| | | | |
|---|---|---|---|
| 4,198,957 A | 4/1980 | Cage et al. | |
| 4,485,810 A | 12/1984 | Beard | |
| 4,534,347 A | 8/1985 | Taylor | |
| 4,622,966 A | 11/1986 | Beard | |
| 4,633,880 A | 1/1987 | Osypka et al. | |
| 4,862,890 A | 9/1989 | Stasz et al. | |
| 5,013,312 A | 5/1991 | Parins et al. | |
| 5,085,659 A | 2/1992 | Rydell | |
| 5,176,702 A * | 1/1993 | Bales | A61B 17/29 81/319 |
| 5,275,608 A * | 1/1994 | Forman | A61B 17/29 606/205 |
| 5,300,068 A | 4/1994 | Rosar et al. | |
| 5,360,428 A | 11/1994 | Hutchinson, Jr. | |
| 5,395,367 A * | 3/1995 | Wilk | A61B 17/00234 606/1 |
| 5,441,499 A | 8/1995 | Fritzsch | |
| 5,454,827 A * | 10/1995 | Aust | A61B 1/0052 606/174 |
| 5,467,763 A * | 11/1995 | McMahon | A61B 17/29 606/208 |
| 5,490,819 A * | 2/1996 | Nicholas | A61B 1/32 606/205 |
| 5,514,157 A * | 5/1996 | Nicholas | A61B 17/0218 606/198 |
| 5,520,678 A * | 5/1996 | Heckele | A61B 34/71 606/1 |
| 5,531,744 A | 7/1996 | Nardella et al. | |
| 5,536,267 A | 7/1996 | Edwards et al. | |
| 5,540,706 A * | 7/1996 | Aust | A61B 17/32002 606/180 |
| 5,582,617 A * | 12/1996 | Klieman | A61B 34/71 606/174 |
| 5,599,295 A | 2/1997 | Rosen et al. | |
| 5,599,346 A | 2/1997 | Edwards et al. | |
| 5,611,798 A | 3/1997 | Eggers | |
| 5,693,044 A * | 12/1997 | Cosmescu | A61B 18/042 606/49 |
| 5,702,408 A * | 12/1997 | Wales | A61B 17/07207 606/205 |
| 5,752,951 A * | 5/1998 | Yanik | A61B 18/1445 606/41 |
| 5,849,011 A * | 12/1998 | Jones | A61B 18/1477 606/49 |
| 5,916,146 A * | 6/1999 | Allotta | A61B 34/71 600/141 |
| 6,027,501 A | 2/2000 | Goble et al. | |
| 6,113,599 A * | 9/2000 | Landsberger | A61B 17/663 606/57 |
| 6,190,385 B1 * | 2/2001 | Tom | A61B 18/14 439/502 |
| 6,217,528 B1 | 4/2001 | Koblish et al. | |
| 6,361,532 B1 * | 3/2002 | Burek | A61B 18/1402 606/49 |
| 6,494,881 B1 | 12/2002 | Bales et al. | |
| 6,530,924 B1 | 3/2003 | Ellman et al. | |
| 6,533,781 B2 | 3/2003 | Heim et al. | |
| 6,752,767 B2 | 6/2004 | Turovskiy et al. | |
| 7,033,354 B2 | 4/2006 | Keppel | |
| 7,371,234 B2 | 5/2008 | Young | |
| 7,399,299 B2 | 7/2008 | Daniel et al. | |
| 7,419,488 B2 | 9/2008 | Ciarrocca et al. | |
| 7,846,108 B2 | 12/2010 | Turovskiy et al. | |
| 7,846,158 B2 | 12/2010 | Podhajsky | |
| 8,137,345 B2 | 3/2012 | McNall, III et al. | |
| 8,968,301 B2 | 3/2015 | Weber | |
| 9,060,765 B2 | 6/2015 | Rencher et al. | |
| 9,358,065 B2 | 6/2016 | Ladtkow et al. | |
| 9,445,863 B2 | 9/2016 | Batchelor et al. | |
| 9,775,665 B2 | 10/2017 | Ellman | |
| 9,883,880 B2 * | 2/2018 | Malkowski | A61B 17/29 |
| 9,993,287 B2 | 6/2018 | Sartor et al. | |
| 10,045,761 B2 | 8/2018 | Weber | |
| 10,322,281 B2 * | 6/2019 | Zhang | A61B 1/0055 600/114 |
| 10,376,314 B2 | 8/2019 | van der Weide et al. | |
| 10,426,546 B2 * | 10/2019 | Graham | A61B 17/29 606/205 |
| 10,433,898 B2 | 10/2019 | Borgmeier et al. | |
| 10,433,899 B2 | 10/2019 | Borgmeier et al. | |
| 10,531,917 B2 | 1/2020 | Johnson et al. | |
| 2002/0022838 A1 * | 2/2002 | Cunningham | A61B 18/042 606/49 |
| 2004/0236316 A1 * | 11/2004 | Danitz | A61B 34/70 606/1 |
| 2005/0070895 A1 | 3/2005 | Ryan et al. | |
| 2005/0107667 A1 * | 5/2005 | Danitz | A61B 34/70 600/139 |
| 2005/0273084 A1 * | 12/2005 | Hinman | A61B 17/00 606/1 |
| 2005/0273085 A1 * | 12/2005 | Hinman | A61B 17/29 606/1 |
| 2005/0283149 A1 | 12/2005 | Thorne et al. | |
| 2006/0020287 A1 * | 1/2006 | Lee | A61B 17/29 606/205 |
| 2006/0111209 A1 * | 5/2006 | Hinman | A61B 17/28 474/206 |
| 2006/0111210 A1 * | 5/2006 | Hinman | A61B 17/32 474/206 |
| 2006/0111615 A1 * | 5/2006 | Danitz | A61B 1/0055 600/114 |
| 2006/0178667 A1 * | 8/2006 | Sartor | A61B 18/1402 606/42 |
| 2007/0078454 A1 | 4/2007 | McPherson | |
| 2007/0118110 A1 | 5/2007 | Girard et al. | |
| 2007/0149966 A1 | 6/2007 | Dahla et al. | |
| 2007/0179494 A1 | 8/2007 | Faure | |
| 2007/0198009 A1 * | 8/2007 | MacDonald | A61B 18/1402 606/45 |
| 2007/0219546 A1 | 9/2007 | Mody et al. | |
| 2007/0260240 A1 | 11/2007 | Rusin | |
| 2007/0265609 A1 | 11/2007 | Thapliyal et al. | |
| 2007/0282371 A1 * | 12/2007 | Lee | A61B 17/29 606/205 |
| 2008/0015631 A1 * | 1/2008 | Lee | A61B 1/0052 606/205 |
| 2008/0046000 A1 * | 2/2008 | Lee | A61B 17/29 606/205 |
| 2008/0058595 A1 * | 3/2008 | Snoke | A61B 1/018 600/114 |
| 2008/0281323 A1 | 11/2008 | Burbank et al. | |
| 2008/0312668 A1 * | 12/2008 | Grace | A61B 34/75 606/147 |
| 2009/0069804 A1 * | 3/2009 | Jensen | A61B 18/1815 606/41 |
| 2009/0138006 A1 * | 5/2009 | Bales | A61B 18/1206 606/33 |
| 2009/0248017 A1 * | 10/2009 | Heard | A61B 18/1477 606/42 |
| 2009/0306642 A1 | 12/2009 | Vankov | |
| 2010/0010512 A1 * | 1/2010 | Taylor | A61B 17/0491 606/144 |
| 2010/0041945 A1 * | 2/2010 | Isbell, Jr. | A61B 17/29 600/142 |
| 2010/0217284 A1 * | 8/2010 | Grace | A61B 34/37 606/147 |
| 2010/0286480 A1 * | 11/2010 | Peine | A61B 17/062 600/131 |
| 2011/0184459 A1 * | 7/2011 | Malkowski | A61B 18/1445 606/206 |
| 2011/0230875 A1 * | 9/2011 | Walberg | A61B 18/1445 606/33 |
| 2012/0116416 A1 | 5/2012 | Neff et al. | |
| 2012/0330307 A1 * | 12/2012 | Ladtkow | A61B 18/1482 606/42 |
| 2013/0023911 A1 * | 1/2013 | Esanu | A61B 17/29 606/151 |
| 2013/0023924 A1 * | 1/2013 | Mueller | A61B 17/29 606/205 |

(56) References Cited

U.S. PATENT DOCUMENTS

| | | | | |
|---|---|---|---|---|
| 2013/0304049 A1* | 11/2013 | Behnke, II | | A61B 18/1206 |
| | | | | 606/34 |
| 2013/0331830 A1* | 12/2013 | Podhajsky | | A61B 18/18 |
| | | | | 606/29 |
| 2014/0121595 A1* | 5/2014 | Tegg | | A61M 25/0147 |
| | | | | 604/95.04 |
| 2014/0257276 A1* | 9/2014 | Sartor | | A61B 18/042 |
| | | | | 606/41 |
| 2015/0359585 A1* | 12/2015 | Weber | | A61B 18/1402 |
| | | | | 606/49 |
| 2016/0074028 A1* | 3/2016 | Castro | | A61B 18/1442 |
| | | | | 606/130 |
| 2016/0143658 A1* | 5/2016 | Stokes | | A61B 17/320092 |
| | | | | 606/169 |
| 2016/0310816 A1* | 10/2016 | Horne | | A63B 23/03516 |
| 2016/0331455 A1* | 11/2016 | Hancock | | A61B 18/1815 |
| 2017/0105782 A1* | 4/2017 | Scheib | | A61B 18/1445 |
| 2017/0105786 A1* | 4/2017 | Scheib | | A61B 17/07207 |
| 2017/0181604 A1* | 6/2017 | Schena | | A61B 34/20 |
| 2017/0245933 A1* | 8/2017 | Graham | | A61B 18/1482 |
| 2017/0273733 A1* | 9/2017 | Weber | | A61B 18/1402 |
| 2017/0325886 A1* | 11/2017 | Graham | | A61B 18/148 |
| 2018/0078301 A1* | 3/2018 | Vayser | | A61B 90/30 |
| 2018/0132850 A1* | 5/2018 | Leimbach | | A61B 90/96 |
| 2018/0333195 A1* | 11/2018 | Greep | | A61B 18/148 |
| 2018/0353162 A1* | 12/2018 | Hancock | | A61B 18/1815 |
| 2019/0083172 A1 | 3/2019 | Ladtkow et al. | | |
| 2019/0125361 A1* | 5/2019 | Shelton, IV | | A61B 17/32 |
| | | | | 474/206 |
| 2019/0125454 A1* | 5/2019 | Stokes | | A61B 17/29 |
| | | | | 606/1 |
| 2019/0125476 A1* | 5/2019 | Shelton, IV | | A61B 17/282 |
| 2019/0175257 A1* | 6/2019 | Tanaka | | A61B 34/71 |
| | | | | 600/141 |
| 2019/0201021 A1* | 7/2019 | Shelton, IV | | A61B 34/70 |
| | | | | 600/139 |
| 2019/0201137 A1* | 7/2019 | Shelton, IV | | A61B 34/70 |
| | | | | 606/1 |
| 2019/0201139 A1* | 7/2019 | Shelton, IV | | A61B 17/28 |
| | | | | 474/206 |
| 2019/0206565 A1* | 7/2019 | Shelton, IV | | A61B 1/0052 |
| | | | | 606/205 |
| 2021/0121226 A1* | 4/2021 | Joseph | | A61B 17/29 |
| | | | | 606/208 |
| 2021/0196356 A1* | 7/2021 | Shelton, IV | | A61B 17/32002 |
| | | | | 606/180 |
| 2021/0386473 A1* | 12/2021 | Baril | | A61B 18/1402 |
| | | | | 606/42 |

\* cited by examiner

ARTICULATING TIP FOR BIPOLAR PENCIL

BACKGROUND

Technical Field

The present disclosure relates generally to electrosurgical instruments and, more particularly, to an articulating tip for an electrosurgical bipolar pencil configured for bipolar resection.

Background of Related Art

Electrosurgical instruments have become widely used by surgeons in recent years. Accordingly, a need has developed for equipment and instruments which are easy to handle, are reliable and are safe in an operating environment. By and large, most electrosurgical instruments are hand-held instruments, e.g., an electrosurgical pencil, which transfer radio-frequency (RF) electrical or electrosurgical energy to a tissue site. The electrosurgical energy is returned to the electrosurgical source via a return electrode pad positioned under a patient (i.e., a monopolar system configuration) or a smaller return electrode positionable in bodily contact with or immediately adjacent to the surgical site (i.e., a bipolar system configuration). The waveforms produced by the RF source yield a predetermined electrosurgical effect known generally as electrosurgical coagulation, electrosurgical sealing, electrosurgical cutting, and/or electrosurgical fulguration or, in some instances, an electrosurgical blend thereof.

In particular, electrosurgical fulguration includes the application of an electric spark to biological tissue, for example, human flesh or the tissue of internal organs, without significant cutting. The spark is produced by bursts of radio-frequency electrical or electrosurgical energy generated from an appropriate electrosurgical generator. Coagulation is defined as a process of desiccating tissue wherein the tissue cells are ruptured and dehydrated/dried. Electrosurgical cutting/dissecting, on the other hand, includes applying an electrical spark to tissue in order to produce a cutting, dissecting and/or dividing effect. Blending includes the function of cutting/dissecting combined with the production of a hemostasis effect. Meanwhile, sealing/hemostasis is defined as the process of liquefying the collagen in the tissue so that it forms into a fused mass.

As used herein the term "electrosurgical pencil" is intended to include instruments that have a handpiece which is attached to an active electrode and that is used to cauterize, coagulate and/or cut tissue. Typically, the electrosurgical pencil may be operated by a handswitch or a foot switch.

As mentioned above, the handpiece of the electrosurgical pencil is connected to a suitable electrosurgical energy source (e.g., generator) that produces the radio-frequency electrical energy necessary for the operation of the electrosurgical pencil. In general, when an operation is performed on a patient with an electrosurgical pencil in a monopolar mode, electrical energy from the electrosurgical generator is conducted through the active electrode to the tissue at the site of the operation and then through the patient to a return electrode. The return electrode is typically placed at a convenient place on the patient's body and is attached to the generator by a conductive material. Typically, the surgeon activates the controls on the electrosurgical pencil to select the modes/waveforms to achieve a desired surgical effect. Typically, the "modes" relate to the various electrical waveforms, e.g., a cutting waveform has a tendency to cut tissue, a coagulating wave form has a tendency to coagulate tissue, and a blend wave form tends to be somewhere between a cut and coagulate wave from. The power or energy parameters are typically controlled from outside the sterile field which requires an intermediary like a circulating nurse to make such adjustment.

When an operation is performed on a patient with an electrosurgical pencil in a bipolar mode, the electrode face includes at least one pair of bipolar electrodes and electrical energy from the electrosurgical generator is conducted through tissue between the pair of bipolar electrodes.

A typical electrosurgical generator has numerous controls for selecting an electrosurgical output. For example, the surgeon can select various surgical "modes" to treat tissue: cut, blend (blend levels 1-3), low cut, desiccate, fulgurate, spray, etc. The surgeon also has the option of selecting a range of power settings typically ranging from 1-300 W. As can be appreciated, this gives the surgeon a great deal of variety when treating tissue. Surgeons typically follow preset control parameters and stay within known modes and power settings and electrosurgical pencils include simple and ergonomically friendly controls that are easily selected to regulate the various modes and power settings Electrosurgical instruments are typically configured such that power output can be adjusted without the surgeon having to turn his or her vision away from the operating site and toward the electrosurgical generator.

SUMMARY

As used herein, the term "distal" refers to the portion that is described which is further from a user, while the term "proximal" refers to the portion that is being described which is closer to a user. The terms "substantially" and "approximately," as utilized herein, account for industry-accepted material, manufacturing, measurement, use, and/or environmental tolerances. Further, any or all of the aspects and features described herein, to the extent consistent, may be used in conjunction with any or all of the other aspects and features described herein.

Provided in accordance with aspects of the present disclosure is an electrode assembly for an electrosurgical pencil, including an insulative housing having a longitudinal axis defined therethrough. A locking plate is supported at a distal end of the insulative housing about a pivot, the locking plate including a series of locking holes defined therein. A tip assembly is coupled to a distal end of the locking plate and is configured to treat tissue. A coaxial connection is coupled to a proximal end of the insulative housing and is electrically coupled to the tip assembly. One or more locking fingers is operably disposed within the housing and is movable between a first position allowing rotation of the locking plate and the tip assembly relative to the longitudinal axis about the pivot and a second position preventing rotation of the locking plate and the tip assembly about the pivot, wherein the one or more fingers is configured to engage a corresponding one of the series of locking holes to prevent rotation of the locking plate and the tip assembly about the pivot.

In aspects according to the present disclosure, two opposing locking fingers are operably disposed within the housing and are movable between respective first and second positions to selectively engage corresponding pairs of locking holes defined in opposite sides of the locking plate. In other aspects according to the present disclosure, the one or more fingers is resilient. In still other aspects according to the present disclosure, the locking holes are arranged on the locking plate in an arcuate fashion.

In aspects according to the present disclosure, the locking plate is pivotable in either direction about the longitudinal axis within the range of about 0 degrees to about 30 degrees. In other aspects according to the present disclosure, the locking plate is U-shaped. In still other aspects according to the present disclosure, the tip assembly includes an active wire and a ground return electrode.

In aspects according to the present disclosure, the tip assembly includes a ceramic core operably coupled to the locking plate, the ceramic core supporting an active electrode wire about a periphery thereof and a ground electrode on one or both sides thereof. In other aspects according to the present disclosure, a coaxial connector is operably coupled to the insulative housing and wherein the active electrode wire operably connects to a center core of the coaxial connector and the ground electrode operably connects to a concentric sleeve defined therethrough. In still other aspects according to the present disclosure, the active wire is made from tungsten or stainless steel.

BRIEF DESCRIPTION OF THE DRAWINGS

The accompanying drawings, which are incorporated in and constitute a part of this specification, illustrate embodiments of the invention, and together with a general description of the invention given above, and the detailed description of the embodiments given below, serve to explain the principles of the invention.

FIG. 5C is an enlarged, top view of the end effector assembly of FIG. 5A shown in a first articulated position;

FIG. 5D is an enlarged, top view of the end effector assembly of FIG. 5A shown in a second articulated position.

DETAILED DESCRIPTION

Figure 1:
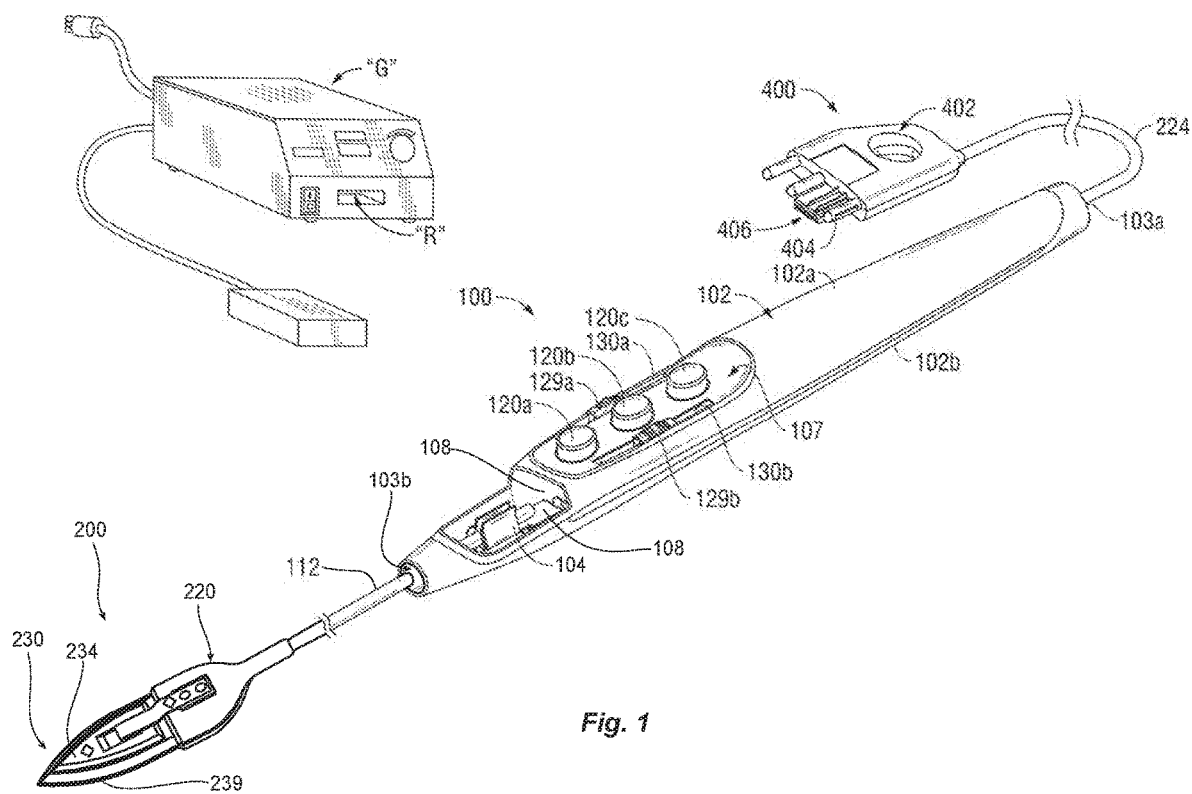
FIG. 1 is a perspective view of a commonly-owned electrosurgical system including an electrosurgical pencil including a housing having a shaft extending therefrom with an end effector attached to a distal end thereof, the end effector configured for bipolar resection in accordance with an embodiment of the present disclosure.

Particular embodiments of the presently disclosed electrosurgical pencil configured for bipolar resection are described in detail with reference to the drawing figures wherein like reference numerals identify similar or identical elements. As used herein, the term "distal" refers to that portion which is further from the user while the term "proximal" refers to that portion which is closer to the user or clinician. The term "leading edge" refers to the most forward edge with respect to the direction of travel while the term "trailing edge" refers to the edge opposite the leading edge with respect to the direction of travel.

FIG. 1 sets forth a perspective view of an electrosurgical system including a commonly-owned electrosurgical pencil 100 constructed for bipolar resection in accordance with one embodiment of the present disclosure. While the following description is directed towards electrosurgical pencils for bipolar resection, the features and concepts (or portions thereof) of the present disclosure may be applied to any electrosurgical type instrument, e.g., forceps, suction coagulators, vessel sealers, wands, etc. The construction, functionality and operation of electrosurgical pencils, with respect to use for bipolar resection, is described herein. Further details of the electrosurgical pencil are provided in commonly-owned U.S. patent application Ser. No. 16/540, 593 filed Aug. 14, 2019 by Baril et al., the entire contents of which being incorporated by reference herein.

The general functions and elements of the prior art, commonly-owned electrosurgical pencil 100 are discussed herein with reference to FIGS. 1-4 of the above-mentioned prior disclosure U.S. patent application Ser. No. 16/540,593. Electrosurgical pencil 100 includes an elongated housing 102 having a top-half shell portion 102a and a bottom-half shell portion 102b. The elongated housing 102 includes a distal opening 103b, through which a shaft 112 of an end effector assembly 200 extends, and a proximal opening 103a, through which connecting wire 224 (see FIG. 1) extends. Top-half shell portion 102a and bottom-half shell portion 102b may be bonded together using any suitable method, e.g., sonic energy, adhesives, snap-fit assemblies, etc.

Electrosurgical pencil 100 further includes a shaft receptacle 104 disposed at a distal end 103b of housing 102 that is configured to receive the shaft 112 of the selectively removable end effector assembly 200. Electrode assembly 200 is configured to electrically connect to generator "G" through various electrical conductors (not shown) formed in the shaft 112, elongated housing 102, connecting wire 224 and plug assembly 400. Generator "G" may be incorporated into the elongated housing 102 and powered by an internal energy supply, e.g., battery or other energy storage device, fuel cell or other energy generation device or any other suitable portable power source.

Shaft 112 is selectively retained by shaft receptacle 104 disposed in housing 102. Shaft 112 may include a plurality of conductive traces or wires (not shown) along the length of the shaft 112. The conductive traces or wires may be fabricated from a conductive type material, such as, for example, stainless steel, or shaft may be coated with an electrically conductive material. Shaft receptacle 104 is fabricated from electrically conductive materials or includes electrically conductive contacts configured to couple with the plurality of conductive traces or wires of the shaft 112. Shaft receptacle 104 is electrically connected to voltage divider network 127 (FIGS. 2 and 4) as explained in more detail below. Conductive traces or wires of the shaft 112 electrically connect to the electrode assembly 200 as explained in more detail below.

As seen in FIG. 1, electrosurgical pencil 100 may be coupled to a conventional electrosurgical generator "G" via a plug assembly 400 (see FIG. 3), as will be described in greater detail below.

For the purposes herein, the terms "switch" or "switches" includes electrical actuators, mechanical actuators, electromechanical actuators (rotatable actuators, pivotable actuators, toggle-like actuators, buttons, etc.) or optical actuators.

Figure 2:
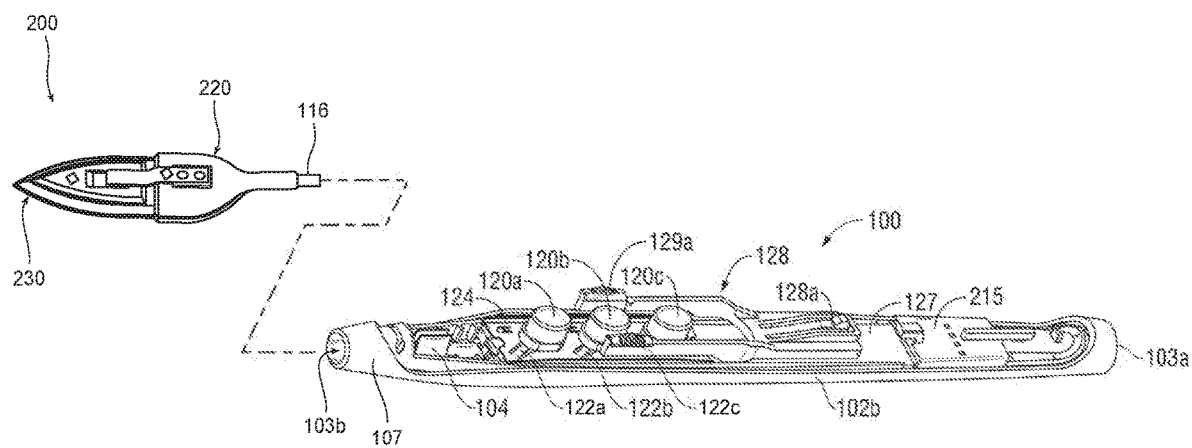
FIG. 2 is a front, top perspective view of the electrosurgical pencil of FIG. 1, with a top-half shell of the housing removed.

Electrosurgical pencil 100 includes one or more activation switches, and may include three activation switches 120a-120c, each of which extends through top-half shell portion 102a of elongated housing 102. Each activation switch 120a-120c is operatively supported on a respective tactile element 122a-122c provided on a switch plate 124, as illustrated in FIG. 2. Each activation switch 120a-120c controls the transmission of RF electrical energy supplied from generator "G" to bipolar electrodes 138 on electrode face 105 of electrode body 112.

More particularly, switch plate 124 is positioned on top of a voltage divider network 127 (hereinafter "VDN 127") such that tactile elements 122a-122c are operatively associated therewith. VDN 127 (e.g., here shown in FIG. 2 as a film-type potentiometer) forms a switch closure. For the purposes herein, the term "voltage divider network" relates to any known form of resistive, capacitive or inductive switch closure (or the like) which determines the output voltage across a voltage source (e.g., one of two impedances) connected in series. A "voltage divider" as used herein relates to a number of resistors connected in series which are provided with taps at certain points to make available a fixed or variable fraction of the applied voltage. Further details of electrosurgical pencil control are provided in above-mentioned U.S. patent application Ser. No. 16/540, 593.

Figure 3:
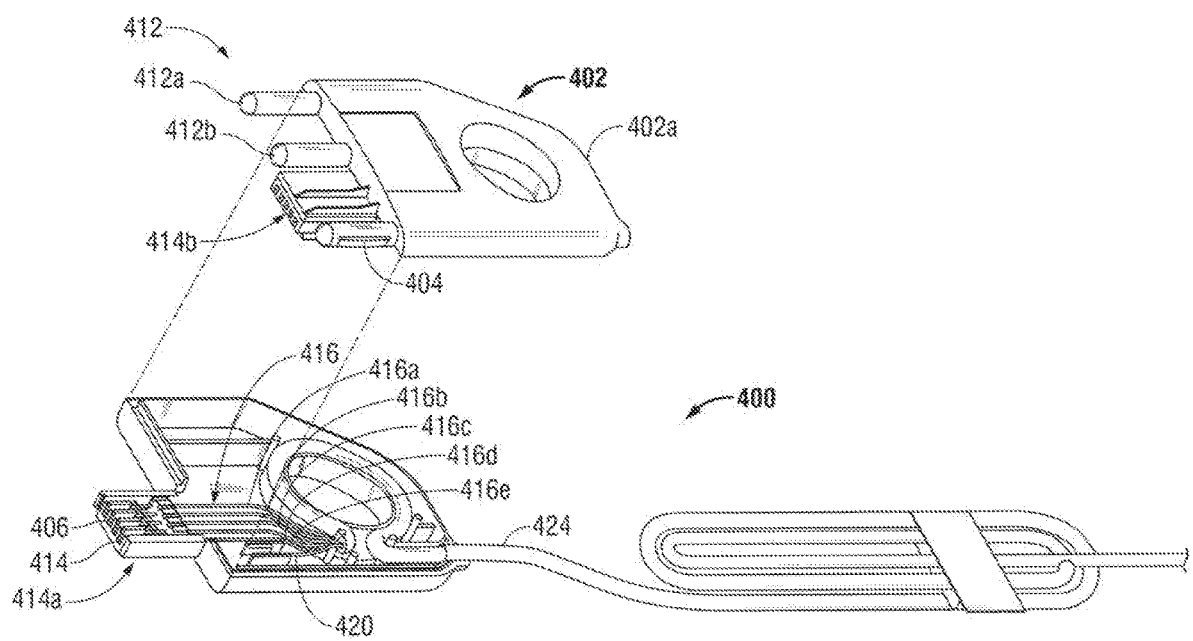
FIG. 3 is a perspective view of the plug assembly of FIG. 1, with a top-half shell section removed therefrom.

In use, depending on which activation switch 120a-120c is depressed a respective tactile element 122a-122c is pressed into contact with VDN 127 and a characteristic signal is transmitted to electrosurgical generator "G" via control wires 416 (see FIG. 3). In one embodiment, three control wires 416a-416c (one for each activation switch 120a-120c, respectively) are provided. Control wires 416a-416c are electrically connected to switches 120a-120c via a control terminal 215 (see FIG. 2) which is operatively connected to VDN 127. By way of example only, electrosurgical generator "G" may be used in conjunction with the device wherein generator "G" includes a circuit for interpreting and responding to the VDN 127 settings.

Activation switches 120a, 120b, 120c are configured and adapted to control the mode and/or "waveform duty cycle" to achieve a desired surgical intent. For example, a first activation switch 120a can be set to deliver a characteristic signal to electrosurgical generator "G" which, in turn, transmits a duty cycle and/or waveform shape that produces a first desirable resection effect. Meanwhile, second activation switch 120b can be set to deliver a characteristic signal to electrosurgical generator "G" which, in turn, transmits a duty cycle and/or waveform shape that produces a second desirable resection effect.

Finally, third activation switch 120c can be set to deliver a characteristic signal to electrosurgical generator "G" which, in turn, transmits a duty cycle and/or waveform shape that produces a third electrosurgical effect/function. Desirable resection effects may include a mode for bipolar coagulation and/or cauterization with an undeployed blade, a mode for bipolar resection with a partially deployed blade, a mode for bipolar resection with a fully deployed blade, a mode for monopolar resection and a mode for resection with blended energy delivery (monopolar and bipolar modes), as will be described in greater detail hereinbelow.

As seen in FIG. 3, fourth and fifth wires (e.g., first RF line 416d and second RF line 416e) are provided and electrically connect to respective active and return electrodes 239, 234 of the end effector assembly 200 (See FIG. 1). Since first RF line 416d and second RF line 416e are directly connected to the end effector assembly 200, first RF line 416d and second RF line 416e bypass the VDN 127 and are isolated from VDN 127 and control wires 416a-416c. By directly connecting the first RF line 416d and second RF line 416e to the end effector assembly 200 (as explained in more detail below) and isolating the VDN 127 from the RF energy transmission, the electrosurgical current does not flow through VDN 127. This, in turn, increases the longevity and life of VDN 127 and/or activation switches 120a, 120b, 120c.

Figure 4:
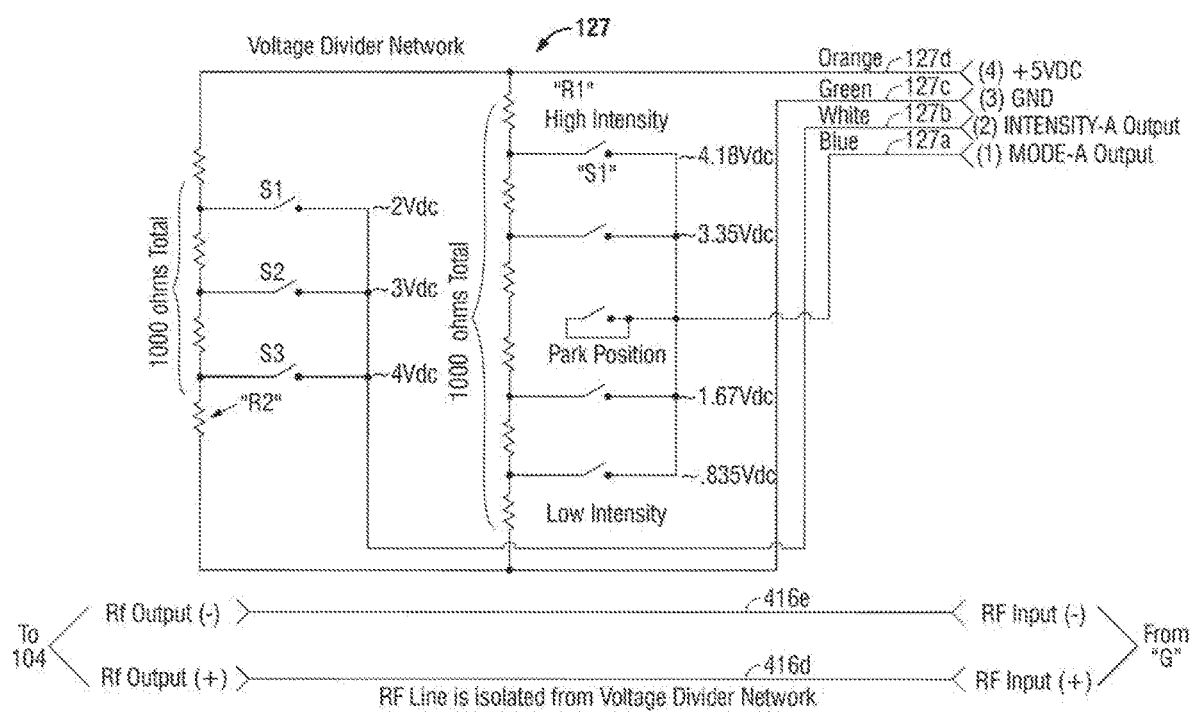
FIG. 4 is a schematic illustration of a voltage divider network for use with the electrosurgical pencil of FIG. 1 and embodiments according to the present disclosure.

With reference to FIG. 4, VDN 127 is shown and includes a first transmission line 127a configured to operate the various modes of electrosurgical pencil 100; a second transmission line 127b configured to operate the various intensities of electrosurgical pencil 100; a third transmission line 127c configured to function as a ground for VDN 127; and a fourth transmission line 127d which transmits up to about +5 volts to VDN 127.

First RF line 416d and second RF line 416e are isolated from or otherwise completely separate from VDN 127. In particular, first RF line 416d and second RF line 416e extends directly from the RF input or generator "G" to the active electrode 239 and return electrodes 234a, 234b of the end effector assembly 200 as explained in more detail below.

By way of example only, VDN 127 may include a plurality of resistors "R1" (e.g., six resistors), connected in a first series between third transmission line 127c and fourth transmission line 127d. The first series of resistors "R1" may combine to total about 1000 ohms of resistance. The first series of resistors "R1" are each separated by a first set of switches "S1". Each switch of the first set of switches "S1" may be electrically connected between adjacent resistors "R1" and first transmission line 127a of VDN 127. In operation, depending on which switch or switches of the first set of switches "S1" is/are closed, a different mode of operation for electrosurgical pencil 100 is activated.

Resection may be performed with electrosurgical energy including waveforms having a duty cycle from about 10% to about 100%. The dual effect of coagulating and cauterizing, as described herein, may be performed with a waveform having a duty cycle from about 10% to about 100%. To increase the depth of coagulation may require a waveform with a duty cycle from about 50% to 100%. It is important to note that these percentages are approximated and may be customized to deliver the desired surgical effect for various tissue types and characteristics.

In one embodiment, the waveforms provided to the bipolar electrosurgical pencil 100 may be dynamically controlled by the generator "G". For example, the mode of operation provided by switches S1, S2, S3 may indicate a range of operation for the generator "G". Generator "G" provides a waveform within the specified range of operation wherein the waveform is dynamically changed based on a parameter, wherein the parameter may be related to one of energy delivery, the target tissue and the duration of energy delivery. The parameter may be obtained from a source external to the generator "G", such as, a measured parameter or clinician provided parameter, or the parameter may include an internal parameter obtained, measured or determined by the generator "G".

As seen throughout FIG. 2, electrosurgical pencil 100 further includes an intensity controller 128 slidingly supported on or in elongated housing 102. Intensity controller 128 may be configured to function as a slide potentiometer, sliding over and along VDN 127 wherein the distal-most position corresponds to a relative high intensity setting, the proximal-most position corresponds to a low intensity settings with a plurality of intermediate positions therebetween. As can be appreciated, the intensity settings from the proximal end to the distal end may be reversed, e.g., high to low.

The intensity settings are typically preset and selected from a look-up table based on a choice of electrosurgical instruments/attachments, desired surgical effect, surgical specialty and/or surgeon preference, the type of end effector assembly 200 and the arrangement of the active and return electrodes 239, 234. The selection of the end effector assembly 200, the intensity setting and duty cycle determines the surgical effect. The settings may be selected manually by the user or automatically. For example, the electrosurgical generator "G" may automatically determine the type of end effector assembly 200 and a predetermined intensity value may be selected and subsequently adjusted by the user or the electrosurgical generator "G".

Turning now to FIG. 3, a detailed discussion of plug assembly 400 is provided. Plug assembly 400 includes a housing portion 402 and a connecting wire 424 that electrically interconnects the housing portion 402 and the control terminal 215 in the electrosurgical pencil 100 (see FIG. 2). Housing portion 402 includes a first half-section 402a and a second half-section 402b operatively engageable with one another, e.g., via a snap-fit engagement. First half-section 402a and second half-section 402b are configured and adapted to retain a common power pin 404 and a plurality of electrical contacts 406 therebetween.

Common power pin 404 of plug assembly 400 extends distally from housing portion 402 at a location between first half-section 402a and second half-section 402b. Common power pin 404 may be positioned to be off center, i.e., closer to one side edge of housing portion 402 than the other. Plug assembly 400 further includes at least one a pair of position pins 412 also extending from housing portion 402. Position pins 412 may be positioned between the first half-section 402a and the second half-section 402b of housing portion 402 and are oriented in the same direction as common power pin 404.

A first position pin 412a is positioned in close proximity to a center of housing portion 402 and a second position pin 412b is positioned to be off center and in close proximity to an opposite side edge of housing portion 402 as compared to common power pin 404. First position pin 412a, second position pin 412b and common power pin 404 may be located on housing portion 402 at locations which correspond to pin receiving positions (not shown) of a connector receptacle "R" of electrosurgical generator "G" (see FIG. 1).

Plug assembly 400 further includes a prong 414 extending from housing portion 402. In particular, prong 414 includes a body portion 414a extending from second half-section 402b of housing portion 402 and a cover portion 414b extending from first half-section 402a of housing portion 402. In this manner, when the first half-section 402a and the second half-section 402b are joined to one another, cover portion 414b of prong 414 encloses the body portion 414a. Prong 414 may be positioned between common power pin 404 and first position pin 412a. Prong 414 is configured and adapted to retain electrical contacts 406 therein such that a portion of each electrical contact 406 is exposed along a front or distal edge thereof. While five electrical contacts 406 are shown, any number of electrical contacts 406 can be provided, including and not limited to two, six and eight. Prong 414 may be located on housing portion 402 at a location that corresponds to a prong receiving position (not shown) of connector receptacle "R" of electrosurgical generator "G" (see FIG. 1).

Since prong 414 extends from second half-section 402b of housing portion 402, housing portion 402 of plug assembly 400 will not enter connector receptacle "R" of electrosurgical generator "G" unless housing portion 402 is in a proper orientation. In other words, prong 414 functions as a polarization member. This ensures that common power pin 404 is properly received in connector receptacle "R" of electrosurgical generator "G".

Connecting wire 424 includes a power supplying wire 420 electrically connected to common power pin 404, control wires 416a-416c electrically connected to a respective electrical contact 406, and first RF line 416d and second RF line 416e electrically connected to a respective electrical contact 406.

Turning to FIG. 5A-5E, another embodiment of an end effector assembly is shown for use with electrosurgical pencil 100 and is resented as end effector assembly 300. End effector 300 includes a shaft 312 (FIG. 5B) having an exposed proximal portion 314 configured to mechanically and electrically engage an active electrical connection 108 of pencil 100 (See FIG. 1). A more distal portion of shaft 312 is configured to engage a shaft receptacle 104 which ultimately connects to a electrical ground. A plurality of suitable electrical connections may be disposed within housing 102 to facilitate the delivery of electrosurgical energy from the electrosurgical generator "G" (See FIG. 1) to an active electrode 379 and return or ground electrode 374 (FIG. 5B) of tip assembly 375.

Shaft 312 is coaxial, i.e., shaft 312 is configured to include both an active connection and a ground return connection. Specifically, a proximal-most tip of shaft 312 includes the exposed active pin 314 which is then concentrically-insulated from the outer ground connection or sleeve 340 that connects to receptacle 104. Further insulation (not shown) surrounds the ground connection. Active pin 314 is configured to electrically and mechanically engage electrical connector 108 and outer ground connection 340 is configured to electrically and mechanically engage shaft receptacle 104.

Shaft 312 and/or shaft receptacle 104 may include a locking device, such as, for example, a shaft locking pin that slides into and engages a shaft locking pin receptacle (not explicitly shown). Any suitable securing and/or locking apparatus may be used to releasably secure the shaft 312 to the elongated housing 102. As described herein, the shaft 312 may be interchangeable within a distal end 107 of the elongated housing 102. In other embodiments, shaft 312 is integrated into the elongated housing 102 and is not replaceable.

Turning back to FIGS. 5A and 5B, bipolar tip assembly 375 of electrode assembly 300 includes an insulative support 376, e.g., a ceramic core, configured to support active electrode or active wire 379, e.g., a tungsten wire, around a peripheral surface thereof. Active wire 379 may be crimped or otherwise secured about all or a portion of the ceramic core 376. Active wire 379 electrically couples to active pin 314 which, in turn, electrically couples to contact 108 disposed in housing 102. A ground return plate 374 is disposed along the tip assembly 375 and through electrode assembly 300 for connection to corresponding receptacle 104 disposed in distal opening 103b upon engagement of the end effector assembly 300 with the housing 102 for ultimate connection to a ground (See FIG. 1). Shaft receptacle 104 may include one or more mechanical interfaces, e.g., step-like surfaces, to facilitate engagement of the end effector 300 with housing 102. Contact 108, in turn, operably couples to one or more switches 120a-120c (See FIG. 2) disposed on housing 102 used to activate the generator "G" to energize the electrodes, e.g., active wire 379 and ground return plate 374, in a bipolar manner. The variously described switches 120a-120c with respect to FIGS. 1-4 may also be utilized along with the intensity controllers 129a, 129b associated therewith.

Turning back to FIGS. 5A and 5B, electrode assembly 300 includes an articulation assembly 330 configured to allow mechanical articulation of the tip assembly 375 either prior to use or during use thereof. Articulation assembly 330 includes a U-shaped articulation or locking plate 331 pivotably mounted to housing 320 via pivot 345 and attached at a distal surface thereof to the tip assembly 375. Pivot 345 allows the tip assembly 375 to be articulated toward the left "RL" or to the right "RR" depending upon a particular purpose. The tip assembly 375 may be articulated in the direction "RL" at an angle alpha ($\lambda$) in the range of about 0 to about 30 degrees. The tip assembly 375 may be articulated in the direction "RR" at an angle beta ($\beta$) in the range of about 0 to about 30 degrees.

U-shaped plate 331 includes a series of locking holes 335a-335e defined in each side of the plate 331 that are configured to align in transverse pairs on either side of the pivot 345. The holes 335a-335e may be defined in the locking plate 331 in an arcuate manner. A pair of resilient locking fingers 332a and 332b extends distally from housing 320 and is configured to engage locking holes 335a-335e to lock the tip assembly 375 at an angle alpha ($\lambda$) or an angle beta ($\beta$) depending upon a particular purpose. More particularly, each locking finger 332a, 332b includes a substantially right angled hook portion 334a and 334b that extends transversally relative to a longitudinal axis "A" defined through the electrode assembly 300 (FIGS. 5C and 5D). Each hook portion 334a and 334b is configured to engage one of a respective pair of locking holes, e.g., locking holes 335c, to lock the plate 331 at a specific angle alpha ($\lambda$) or angle beta ($\beta$).

Each hook portion 334a and 334b is configured to resiliently flex inwardly under a bias toward axis "A" to allow selective release of plate 331 therefrom and allow manual rotation of the plate 331 and tip assembly 375 to a desired angle alpha ($\lambda$) or an angle beta ($\beta$). Once the tip assembly 375 is at the desired angle, the hook portions 334a and 334b may be released which causes the hook portions 334a and 334b to flex outwardly relative to axis "A" to engage a corresponding pair of opposing locking holes, e.g., locking holes 335d.

Figure 5A:
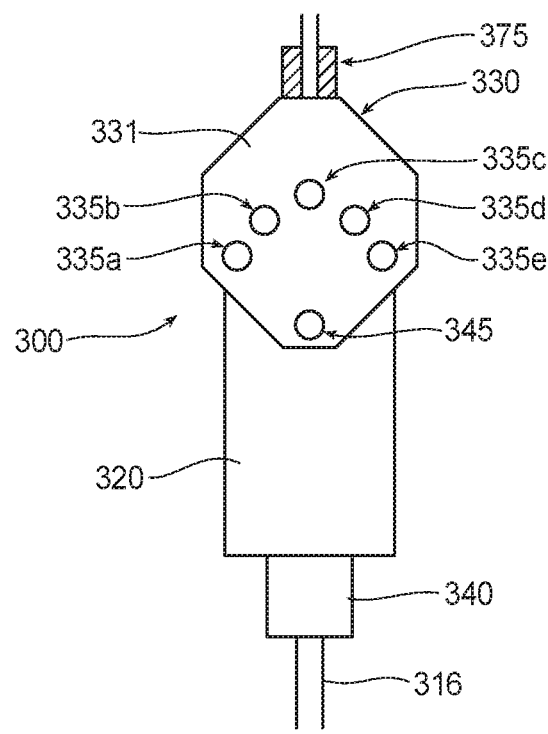
FIG. 5A is an enlarged, top view of one embodiment of an end effector assembly according to the present disclosure.
Figure 5B:
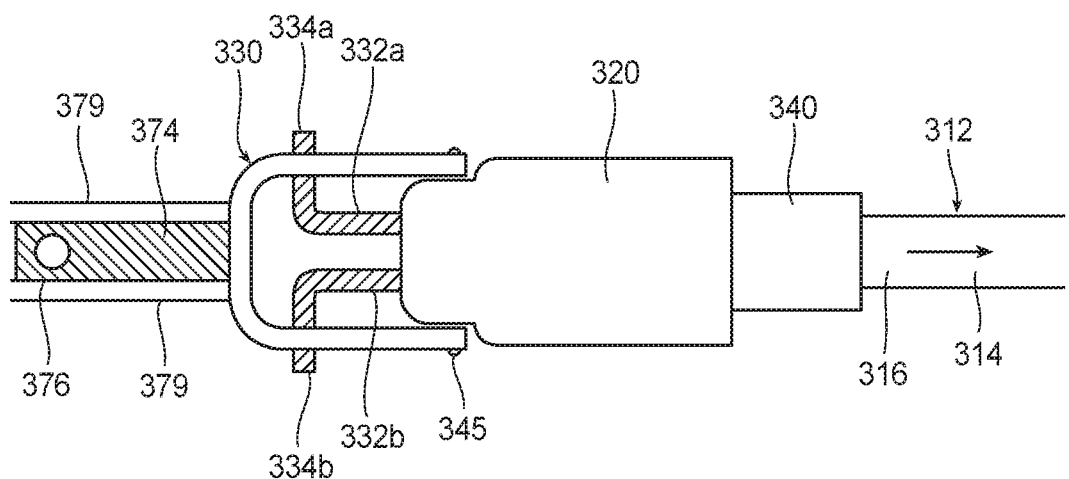
FIG. 5B is an enlarged, side view of the end effector assembly of FIG. 5A.
Figure 5E:
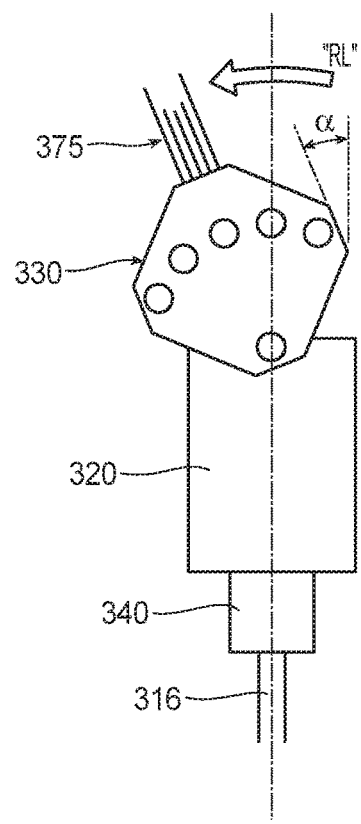
FIG. 5E is schematic view of the end effector assembly of FIG. 5A shown in use treating tissue "T".
Figure 5E:
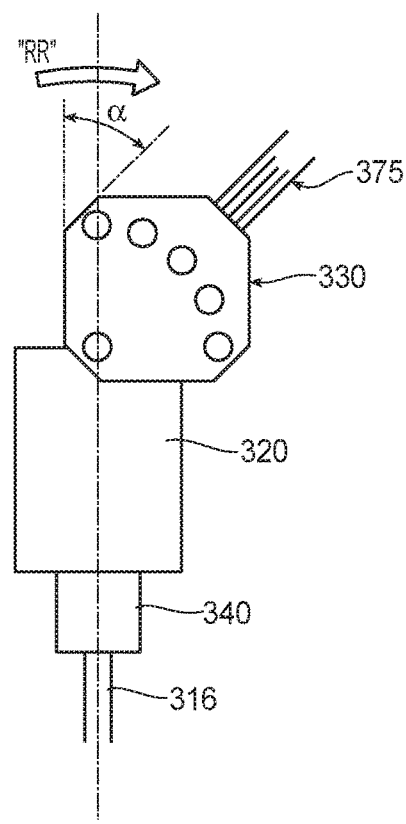
Figure 5E:
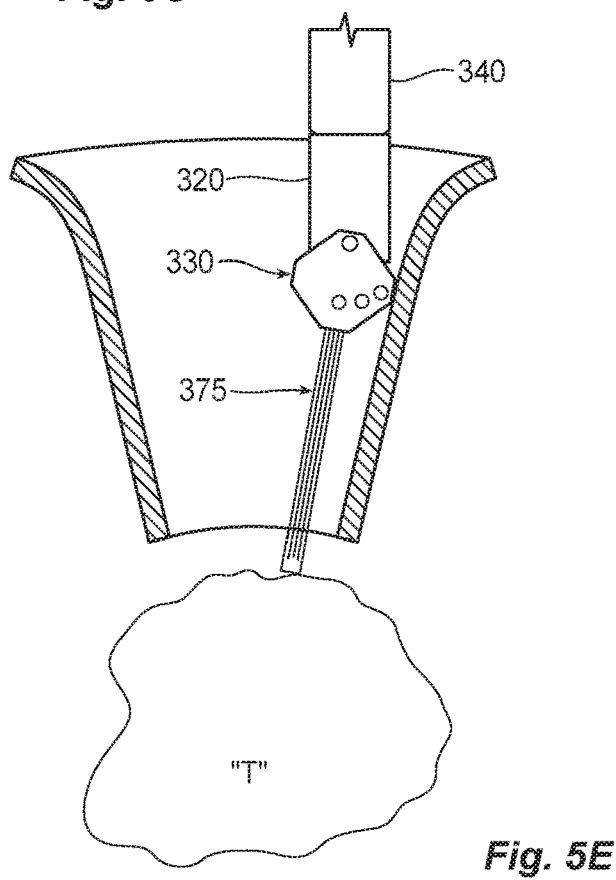

The tip assembly 375 may be oriented to a desired angle alpha ($\lambda$) or an angle beta ($\beta$) prior to surgery or at any time during surgery. Any number of locking holes 335a-335e may be utilized to provide more flexibility and angles of operation to the surgeon. Moreover, the surgeon may opt to maintain the tip assembly 375 at a neutral angle, i.e., wherein the tip assembly 375 remains in-line with axis "A". Angulation of the tip assembly 375 provides better access and visibility to the surgical site and tissue specimens "T" (FIG. 5E).

The various embodiments disclosed herein may also be configured to work with robotic surgical systems and what is commonly referred to as "Telesurgery." Such systems employ various robotic elements to assist the clinician and allow remote operation (or partial remote operation) of surgical instrumentation. Various robotic arms, gears, cams, pulleys, electric and mechanical motors, etc. may be employed for this purpose and may be designed with a robotic surgical system to assist the clinician during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of clinicians may prep the patient for surgery and configure the robotic surgical system with one or more of the instruments disclosed herein while another clinician (or group of clinicians) remotely controls the instruments via the robotic surgical system. As can be appreciated, a highly skilled clinician may perform multiple operations in multiple locations without leaving his/her remote console which can be both economically advantageous and a benefit to the patient or a series of patients.

For a detailed description of exemplary medical work stations and/or components thereof, reference may be made to U.S. Patent Application Publication No. 2012/0116416, and PCT Application Publication No. WO2016/025132, the entire contents of each of which are incorporated by reference herein.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

The invention claimed is:

1. An electrode assembly for an electrosurgical pencil, comprising:
    an insulative housing including a longitudinal axis;
    a locking plate including:
        a first proximal free end pivotably coupled to a first side of a distal end of the insulative housing;
        a second proximal free end opposite the first proximal free end and pivotably coupled to a second side of the distal end of the insulative housing opposite the first side;
        a distal connector portion joining the first and second proximal free ends;
        an inner cavity defined between the distal connector portion and the first and second proximal free ends, wherein at least a portion of the distal end of the insulative housing is received within the inner cavity;

a first series of locking holes defined through a first side of the locking plate; and a second series of locking holes defined through a second side of the locking plate opposite the first side such that the locking holes of the second series of locking holes are aligned with corresponding locking holes of the first series of locking holes;

a tip assembly coupled to a distal end of the locking plate and configured to treat tissue;

a first locking finger extending distally from the distal end of the insulative housing; and a second locking finger extending distally from the distal end of the insulative housing, wherein each of the first and second locking fingers are configured to:

flex outward relative to the longitudinal axis and away from the other locking finger upon release of a biasing force imparted on the first and second locking fingers by the respective first and second sides of the locking plate such that the first and second locking fingers are received through a locking hole of one of the first or second series of locking holes upon rotation of the locking plate to align the first locking finger with a locking hole of the first series of locking holes and the second locking finger with a locking hole of the second series of locking holes that is aligned with the locking hole of the first series of locking holes with which the first locking finger is aligned, thereby preventing rotation of the locking plate and the tip assembly relative to the longitudinal axis; and flex inward toward the longitudinal axis under a bias imparted on the first and second locking fingers by an inner surface of the respective first and second sides of the locking plate such that the first and second locking fingers are not received within any one locking hole of the respective first or second series of locking holes, thereby allowing rotation of the locking plate.

2. The electrode assembly according to claim 1, wherein the first and second locking fingers are resilient.

3. The electrode assembly according to claim 1, wherein the first and second series of locking holes are arranged on the locking plate in an arcuate fashion.

4. The electrode assembly according to claim 1, wherein the locking plate is pivotable in either direction about the longitudinal axis within the range of about 0 degrees to about 30 degrees.

5. The electrode assembly according to claim 1, wherein the locking plate is U-shaped.

6. The electrode assembly according to claim 1, wherein the tip assembly includes an active electrode wire and a ground return electrode.

7. The electrode assembly according to claim 1, wherein the tip assembly includes a ceramic core operably coupled to the locking plate, the ceramic core supporting an active electrode wire about a periphery of the ceramic core and a ground electrode on at least one side of the ceramic core.

8. The electrode assembly according to claim 7, wherein a coaxial connector is operably coupled to the insulative housing and wherein the active electrode wire operably connects to a center core of the coaxial connector and the ground electrode operably connects to a concentric sleeve defined through the coaxial connector.

9. The electrode assembly according to claim 7, wherein the active electrode wire is made from tungsten or stainless steel.

10. The electrode assembly according to claim 1, wherein the first and second locking fingers include:

a first linear portion disposed between the first and second sides of the locking plate and extending distally from the insulative housing parallel to the longitudinal axis; and a second linear portion extending from a distal end of the first linear portion non-parallel to the longitudinal axis, the second linear portion configured to be received through any one locking hole of the first or second series of locking holes upon rotation of the locking plate.

11. The electrode assembly according to claim 10, wherein the second linear portion extends outward from an outer surface of the locking plate when the second linear portion is received through any one locking hole of the first or second series of locking holes.

\* \* \* \* \*